United States Patent
Sardaryan

(10) Patent No.: US 6,340,586 B1
(45) Date of Patent: Jan. 22, 2002

(54) **STRAIN OF THE MICROORGANISM *PENICILLIUM OXALICUM* VAR. ARMENIACA AND ITS APPLICATION**

(76) Inventor: Eduard Sardaryan, Sakařova 1386, 530 09 Pardubice (CZ)

( * ) Notice: Subject to any disclaimer, the term of this patent is extended or adjusted under 35 U.S.C. 154(b) by 0 days.

(21) Appl. No.: 09/646,791
(22) PCT Filed: May 20, 1998
(86) PCT No.: PCT/CZ98/00024
§ 371 Date: Sep. 22, 2000
§ 102(e) Date: Sep. 22, 2000
(87) PCT Pub. No.: WO99/50434
PCT Pub. Date: Oct. 7, 1999

(30) Foreign Application Priority Data

Mar. 30, 1998 (CS) ................................. 970-98

(51) Int. Cl.$^7$ .................................................. C12N 1/14
(52) U.S. Cl. ................. 435/256.3; 435/256.8
(58) Field of Search ............................ 435/256.3, 256.8

(56) References Cited

U.S. PATENT DOCUMENTS 4,379,842 A * 4/1983 Fujiwara et al. .............. 435/58

* cited by examiner

*Primary Examiner*—Herbert J. Lilling
(74) *Attorney, Agent, or Firm*—Oblon, Spivak, McClelland, Maier & Neustadt, P.C.

(57) ABSTRACT

The strain of the microorganism *Penicillium oxalicum* var. Armeniaca CCM 8242 produces an anthraquinonyl carboxylic acid derivative of structural formula (I), which may be used as a colorant, especially as a food colorant or cosmetic colorant.

3 Claims, No Drawings

STRAIN OF THE MICROORGANISM *PENICILLIUM OXALICUM* VAR. ARMENIACA AND ITS APPLICATION

TECHNICAL FIELD

The invention relates to a new strain of a fungus having the property to produce a red colorant which can be applied as a colorant in the food and cosmetic industries.

BACKGROUND ART

In the food and cosmetic industries there exists a need of colorants well soluble in the components of the respective products, the colour of which does not show a bathochromic effect and which is stable at boiling.

DISCLOSURE OF THE INVENTION

The invention consists in the strain *Penicillium oxalicum* var. Armeniaca CCM 8242.

When the strain being described, belonging to the species *Penicillium oxalicum*, was cultivated in a broth, let it be liquid or solid, there was observed already on the second day of incubation increased synthesis of a red colorant which was released into the broth. The yield of the purified red colorant amounts to 1.5 to 2 g from 1 liter of the nutrient broth.

The strain was deposited at the International Depositary Authority CCM—Czech Collection of Microorganisms of the Masaryk University, Tvrdého 14, 602 00 Brno, Czech Republic, on Mar. 19, 1998 under the accession No. CCM 8242.

Said strain forms short conidiophores of dimensions 60 to 70 times 5 to 6 μm. Each broomstick includes from 2 to 7 conidii. The conidii are roundshaped, of a diameter of from 15 to 20 μm, with a smooth yellow-gold surface, and they disintegrate easily during microscopic examination.

In the Czapek's mineral broth, the strain forms standardly growing colonies which achieve 2 to 2.5 cm on the third day of incubation, and up to 4.5 cm on the fifth to sixth day. The colonies are unbooked, velvet-like, the hyphae are short, sporulating, with a fragile surface and they crumble out. When shaking a vessel with a ripe culture, it is characteristic for the conidii that they drop away in bulk. No zone effect is shown. The mycelium is short, of a light green colour which changes in the course of the culture growing to a dark green colour. The white colour of the growing colony edge amounts to the width of 1 to 2 mm. The reverse side of the colony becomes red, and said red colour becomes more intensive during the growing of the culture, and it diffuses into agar, which becomes intensively coloured in a striking red colour.

In the malt agar as an organic broth, the colonies are large, with a short light mycelium coloured green. During the strain growth no biosynthesis of red colour is shown, or it is produced slightly only.

In an organic broth which is represented by a cabbage infusion-agar or a potato infusion-agar, there are formed quickly growing colonies having a diameter of 5 to 7 cm. The mycelium is fragile, green. There appears higher production of yellow-gold conidia. During the growth of the culture, the adverse side of the colony gets a red colouring and the colorant diffuses into the agar which becomes intensively dark red.

The pigmentation of the reverse side of the colony starts on the second day of the strain incubation and achieves its maximum in a seven-day culture. At the broth pH value lower than 3 and higher than 9, at a standard growth of the culture, biosynthesis of the red colorant is stopped or it is produced very slightly. The optimum pH value for producing the red colorant is 5.6 to 6.2. No odour or exudate appears.

The strain hydrolyses starch intensively, it does not dilute gelatin and it does not peptonize milk.

It absorbs organic nitrogen in the form of aminoacids asparagine, valine, serine and tyrosine.

L-(+)-maltose, L-(+)-arabinose, D-(+)-sorbitol and D-(+)-mannitol are excellent sources of saccharidic nutrition.

As to organic acids, it absorbs succinic, lactic and maleic acids.

The optimum temperature for growing fungi and for biosynthesis of the colorant is 27 to 29° C. The production strain is also multiplied at the temperature of 37 to 38° C., and it does not lose the property to form the pigment. The production fungus strain is kept by means of a method of periodic reinoculations in test-tubes in bunches of cabbage agarised broth in a refrigerator at the temperature of +4 to +5° C. The reinoculation period amounts to 2 up to 3 months.

Another aspect of the invention provides a method for the cultivation of the microorganism strain *Penicillium oxalicum* var. Armeniaca, wherein the above mentioned production strain is grown at a temperature of 25 to 30° C., preferably at 27 to 29° C., at a gauge pressure of 50 to 80 kPa (0,5 to 0,8 atm), advantageously with continuous mixing at 280 rpm, with air supplied at a ratio of 1.2 air volumes to 1.0 broth volume, in a broth of pH 3 to 9, preferably of pH 5.8 to 6.2, containing carbohydrates, preferably from 1.5 to 1.8 wt. %, and ammonia nitrogen, preferably from 0.66 to 0.69 wt. %, for 60 to 72 hours, preferably for 64 to 68 hours, and thereafter the liquid is removed from the nutrient broth and the resulting red colorant is isolated from said liquid.

The obtained colorant can be used as a food colorant or a cosmetic colorant.

The colorant is a dark red crystalline powder of a raspberry-red colour in an aqueous solution. No odour or taste appear either in the crystalline form or in the solution.

Its melting point is 127° C. (decomposition). It is not soluble in water, it is soluble in an alkaline solution (pH 9.0 to 9.5) and in ethyl alcohol. It is well soluble in whites of eggs, in fats and in concentrated acetic acid. The colour of the colorant is not changed depending on the pH value, which means that there is no bathochromic effect. It has a high stability as to light and resistance with respect to temperature. No change of colour takes place during boiling in solutions for 5 hours at 100° C. It absorbs light in the visible range ($X_{max}$=435 mm and 502 mm). The proportion of peaks amounts to 1.0 to 1.5.

The analytical results by mass spectroscopy revealed that the produced red colorant comprises anthraquinone derivatives, e.g. a derivative of formula

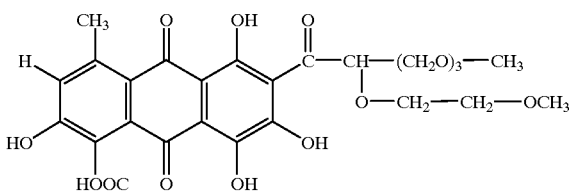

which has the empirical formula $C_{25}H_{26}O_{14}$ and a molecular weight of ca. 550. The ultraviolet, infrared and mass spectra have confirmed an anthraquinone structure.

The multiplication of the culture of the production strain is performed in test tubes with agarised cabbage infusion as the broth by means of the method of periodic reinoculation from operational bunches.

The above broth may be prepared e.g. by the following procedure:

200 to 300 g of finely grated cabbage is added to 1 liter of drinking water and it is boiled for 20 minutes. After cooling down to the temperature of 50° C., the solution is filtered. The filtrate is completed to 1 liter and 20 g of agar-agar is added. The sterilization of the broth takes place at 70 to 80 kPa (0.7 to 0.8 atm) for 20 minutes. The prepared broth is divided per 6 to 8 ml into sterile test tubes dimensioned 18×150 mm at a temperature of 50 to 55° C. and is sterilized in autoclaves under the following conditions: temperature 116° C., steam pressure 100 kPa (1.0 atm), sterilization period 20 min.

After having been sterilized, the test tubes with the agarised slope broth are dried in advance in a thermostat at the temperature of 37° C. for one day. The finished bunches are inoculated with the culture of the production strain and they are let to ripe at the temperature of 27 to 29° C. The incubation period is 5 days.

The active colonies of the microorganisms are harvested by means of further reinoculations of spores in a Petri dish with the agarised cabbage infusion. A basis for the selection of the active colonies is the colouring intensity of the colonies of a minimum diameter of 0.5 to 1 cm, with a smooth surface and with a growing zone of min. 0.1 to 0.2 cm. The active colonies are harvested in the agarised cabbage infusion.

Based on its morphological and cultural properties, the recovered fungus strain is most approaching to the species *Penicillium oxalicum* (according to I. M. Pidoplichko, 1972).

It is possible to perform the cultivation of the production strain of the invention in fermentors, in liquid broths, by means of the submerged method. The quantity of the inoculated material is 3 to 7 wt. %. After the inoculation, operational bunches with a five-day culture incubated in a cabbage infusion are used. The cultivation of the seed material is performed at the temperature of 27 to 29° C. within 64 to 68 hours.

The optimum conditions for performing the procedure of the microbiological synthesis include the temperature of 27 to 29° C., continuous mixing with the peripheral velocity of about 280 $min^{-1}$, supply of air in the proportion of 1.2 air volumes to 1.0 volume of the broth, a gauge pressure in the operational fermentor amounting to 50 to 80 kPa (0.5 to 0.8 atm).

Already after fermenting the production microorganism for 30 to 35 hours, the liquid above the culture becomes red, and the intensity of the red colour is at its maximum—dark cerise colour—after an incubation period of 68 to 72 hours As components of the broth there are used carbohydrates, various saccharides, polyfunctional alcohols and hydrocarbons, and also wastes of sugar production—molasses—in the quantity of 10 to 20 g for 1 liter of water.

For supplying nitrogen, corn extract, yeast autolysate or extract, and also compounds containing nitrogen in various forms (such as amino acids) at a quantity of nitrogen of 0.5 to 0.7 wt. % can be used.

The optimum values of the broth are as follows: pH 5.8 to 6.2, content of carbohydrates 1.5 to 1.8 wt. %., content of ammonia nitrogen 0.66 to 0.69 wt. %.

EXAMPLES

Broth Composition

Example 1

| Granulated sugar | 12 to 20 g/l |
|---|---|
| Corn extract | 5 to 10 g/l |
| Zinc sulfate | 0.002 g/l |
| Magnesium sulfate | 0.001 g/l |

Example 2

| Granulated sugar | 12 to 20 g/l |
|---|---|
| Yeast extract | 5 to 10 g/l |
| Zinc sulfate | 0.002 g/l |
| Magnesium sulfate | 0.001 g/l |

Example 3

| Molasses | 12 to 20 g/l |
|---|---|
| Corn extract or yeast extract or autolysate | 5 to 10 g/l |
| Zinc sulfate | 0.002 g/l |
| Magnesium sulfate | 0.001 g/l |

The broth in the operating fermentor is inocluated with a two-day culture of *Penicillium oxalicum* var. Armeniaca CCM 8242, which has been cultivated in an inoculation device. The quantity of the inoculation material amounts to 3 up to 7 vol. % of the broth.

Separation of the Culture Supenatant from the Fungus Biomass

After biosynthesis of the red colorant is completed, the liquid from the broth is filtered or centrifuged off for being separated from the biomass. For the colorant to be precipitated, the liquid is acidified to pH 3.0 to 2.5. The acidification can be performed by any organic or inorganic acid. The precipitation may be performed with aluminium potassium sulfate $AlK_2(SO_4)_3$. Thus a colorant which is insoluble in bases and alcohols is obtained. It is soluble in an alcaline solution at a pH of 9.0 to 10.0. After the precipitation, the colorant is separated from the liquid by centrifuging.

Example 4

The precipitate is dissolved in ethylalcohol and filtered. The alcohol is removed and the colorant in the crystalline form is obtained.

Example 5

The precipitate is dissolved in an ammonia solution at a pH of 9.0 to 10.0. A 5 to 50% aqueous solution of a red colorant is obtained.

Industrial Applicability

The final product of the technology according to the invention is a red colorant of a microbiological origin, destined for food and cosmetic industries.

What is claimed is:

1. The isolated strain of *Penicillium oxalicum* var. Armeniaca CCM 8242.

2. A method for the cultivation of the strain according to claim 1, characterised in that it is performed at the temperature of 25 to 30° C., at a gauge pressure of 50 to 80 kPa (0.5 to 0.8 atm), in a broth of pH 3 to 9, containing carbohydrates and ammonia nitrogen, for 60 to 72 hours, and the red colorant thus produced is isolated from the nutrient broth.

3. The method according to claim 2, characterised in that the cultivation is performed at the temperature of 27 to 29° C., at a gauge pressure of 50 to 80 kPa (0.5 to 0.8 atm), with continuous mixing at a peripheral speed of 280 rpm, with air supplied at a ratio of 1.2 volumes of air to 1.0 volume of a broth having pH 5.8 to 6.2 and containing from 1.5 to 1.8 wt. % carbohydrates and from 0.66 to 0.69 wt. % ammonia nitrogen, for 64 to 68 hours.

* * * * *